United States Patent
Wong

(10) Patent No.: US 9,973,847 B2
(45) Date of Patent: May 15, 2018

(54) MOBILE DEVICE-BASED STETHOSCOPE SYSTEM

(71) Applicant: Eko Devices, Inc., Berkeley, CA (US)

(72) Inventor: Victor Wong, Moraga, CA (US)

(73) Assignee: EKO DEVICES, INC., Berkeley, CA (US)

( * ) Notice: Subject to any disclaimer, the term of this patent is extended or adjusted under 35 U.S.C. 154(b) by 366 days.

(21) Appl. No.: 14/152,278

(22) Filed: Jan. 10, 2014

(65) Prior Publication Data

US 2015/0201272 A1   Jul. 16, 2015

(51) Int. Cl.
| H04R 1/46 | (2006.01) |
|---|---|
| A61B 7/02 | (2006.01) |
| A61B 7/04 | (2006.01) |

(52) U.S. Cl.
CPC .............. *H04R 1/46* (2013.01); *A61B 7/02* (2013.01); *A61B 7/04* (2013.01); *H04R 2420/07* (2013.01)

(58) Field of Classification Search
CPC ........ H04R 1/46; H04R 2420/07; A61B 7/04; A61B 7/02; A61B 7/045; G10K 11/18; G10K 11/22
USPC .......................................................... 381/67
See application file for complete search history.

(56) References Cited

U.S. PATENT DOCUMENTS

| | | | |
|---|---|---|---|
| 3,247,324 A | 4/1966 | Cefaly et al. | |
| 5,717,769 A * | 2/1998 | Williams ................ | A61B 7/04 381/67 |
| 5,774,563 A * | 6/1998 | DesLauriers ............ | A61B 7/04 381/67 |
| 6,139,505 A * | 10/2000 | Murphy .................. | A61B 5/061 381/67 |
| 6,533,736 B1 | 3/2003 | Moore | |
| 8,491,488 B1 * | 7/2013 | Criley ..................... | A61B 7/04 600/528 |
| 2002/0186850 A1 * | 12/2002 | Deslauriers .............. | A61B 7/04 381/67 |
| 2004/0076303 A1 * | 4/2004 | Vyshedskly .............. | A61B 7/04 381/67 |
| 2007/0273504 A1 * | 11/2007 | Tran ..................... | A61B 5/0022 340/539.12 |
| 2008/0298603 A1 * | 12/2008 | Smith .................... | A61B 7/026 381/67 |
| 2014/0012149 A1 | 1/2014 | Trice | |

OTHER PUBLICATIONS

International Search Report and Written Opinion issued by the U.S. Patent and Trademark Office as International Searching Authority for International Application No. PCT/US14/70476 dated Apr. 30, 2015 (11 pages).

* cited by examiner

Primary Examiner — Davetta W Goins
Assistant Examiner — Daniel Sellers
(74) *Attorney, Agent, or Firm* — Wilmer Cutler Pickering Hale and Dorr LLP

(57) ABSTRACT

A mobile device-based stethoscope system that transmits, records, and analyzes sounds to generate a list of matching conditions and facilitates easy attachment across various electronic medical record platforms and other means of communication. The invention is configured to allow the use of either an integrated wireless stethoscope, or an in-line adapter for a conventional stethoscope. Patient sounds are sent from the selected stethoscope head to the mobile device having a software application that allows for the analysis, attachment, and further manipulation of the data.

14 Claims, 6 Drawing Sheets

MOBILE DEVICE-BASED STETHOSCOPE SYSTEM

FIELD OF THE INVENTION

This invention relates to the expanded use of mobile devices for medical applications. More specifically, it relates to transmitting sound data from a stethoscope to a mobile device.

BACKGROUND

Auscultation, the process of listening to the internal sounds of the body, has historically been performed with acoustic stethoscopes. Many different forms of such a device have existed, most notably those comprised with a two-sided chest piece linked with branched hollow tubing to two separate ear pieces. Such devices use a diaphragm to transmit high frequency sounds to a doctor's ears, and a bell to transmit the low frequency sounds. However, the common acoustic stethoscope lacks the ability to digitize sounds for further medical use.

In recent years, many electronic stethoscope models have appeared in the art. Such devices largely resemble acoustic devices with the major difference being in the head. The electronic heads often have digital displays, and house components for noise amplification and recording. Signals can be sent wirelessly to a computer, and some models allow for the direct recording onto removable memory devices. Some models pair with a smartphone application to display images of recorded sounds that can later be edited and attached to medical records using proprietary software, but these models do not analyze patient sounds to provide decision support. Wireless versions present in the art, which comprise of a head physically removed from the hearing device, also lack this analysis capability. Furthermore, the computer-based medical record systems associated with these electronic stethoscopes also tend to be in competing, proprietary formats, reducing the abilities of doctors to collaborate over large distances. What is proposed then, is a mobile-based electronic stethoscope that can serve as a decision support tool based on an analysis of the sounds and the capability to interact with multiple electronic medical record platforms.

BRIEF SUMMARY OF THE EMBODIMENTS OF THE INVENTION

The present invention comprises a process to use a mobile-based stethoscope to serve as a decision support tool for physicians and effectively document health conditions as facilitated through the use of hardware and software components. It features a stethoscope fitted internally with a system of microphones that can detect high and low frequency body sound. The stethoscope includes the ability to wirelessly transmit the detected sound data to a connected wireless mobile device such as a smartphone. The stethoscope itself may further include both analog and digital listening capabilities such that a doctor can choose from two modes in which to listen to the patient while data is collected to the mobile device.

The chosen hardware piece transmits pertinent data to the mobile device. Our software within the phone converts the sounds into an image, which is then converted into data sets based on numbers. The software features a variety of options to aid the user, including the abilities to record the sound, save the sound, analyze the sound to come up with a list of potential conditions, edit the files to add notes, and send the sound out to services such as email and various types of electronic medical records. The sound is analyzed through a comparison with a database of pre-recorded health conditions, which is continually updated through a machine learning algorithm. The phone application is synced with a computer-based application through the cloud, facilitating ease of use and the collaboration of medical professionals across large distances. Patient data is stored in the cloud and accessible by means of a web interface through which each doctor can access their records anywhere with an Internet connection.

BRIEF DESCRIPTION OF THE DRAWINGS

The invention is illustrated in the figures of the accompanying drawings which are meant to be exemplary and not limiting, which like references are intended to refer to like or corresponding parts, and in which.

DETAILED DESCRIPTION

Figure 1:
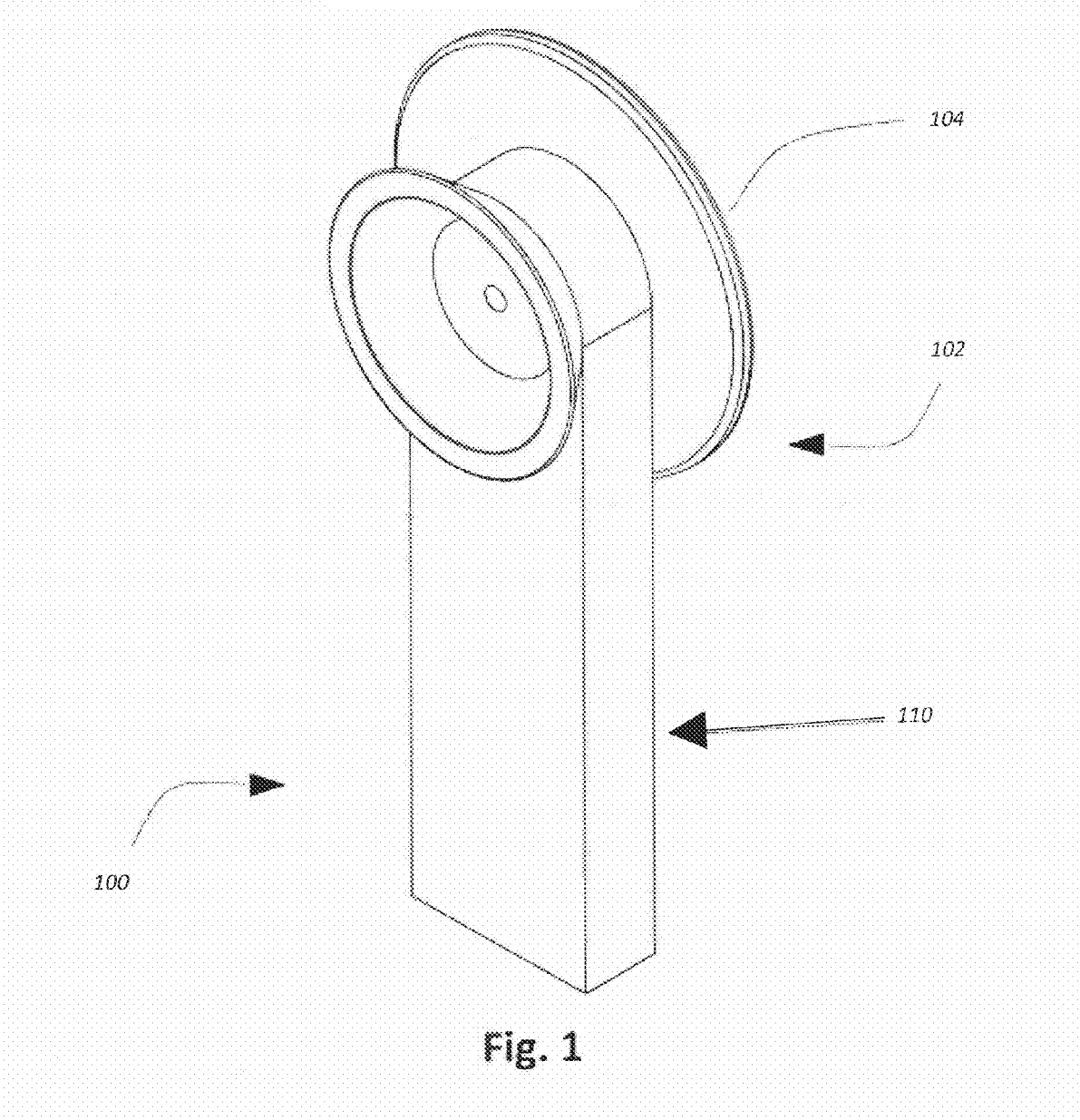
FIG. 1 provides a perspective of a wireless stethoscope model according to one embodiment of the present invention.

FIG. 1 displays a wireless stethoscope 100, which includes a stethoscope head 102 connected to a stethoscope body 110. In the wireless stethoscope model 100, the stethoscope head 102 may be an ordinary acoustic stethoscope with the addition of one or more microphones into the head housing, as described in FIG. 2. The diaphragm 104 is held up to the patient's chest to detect internal body sounds. These sounds are then picked up by the microphone in the head 102 and sent wirelessly to the mobile device for further analysis.

Figure 2:
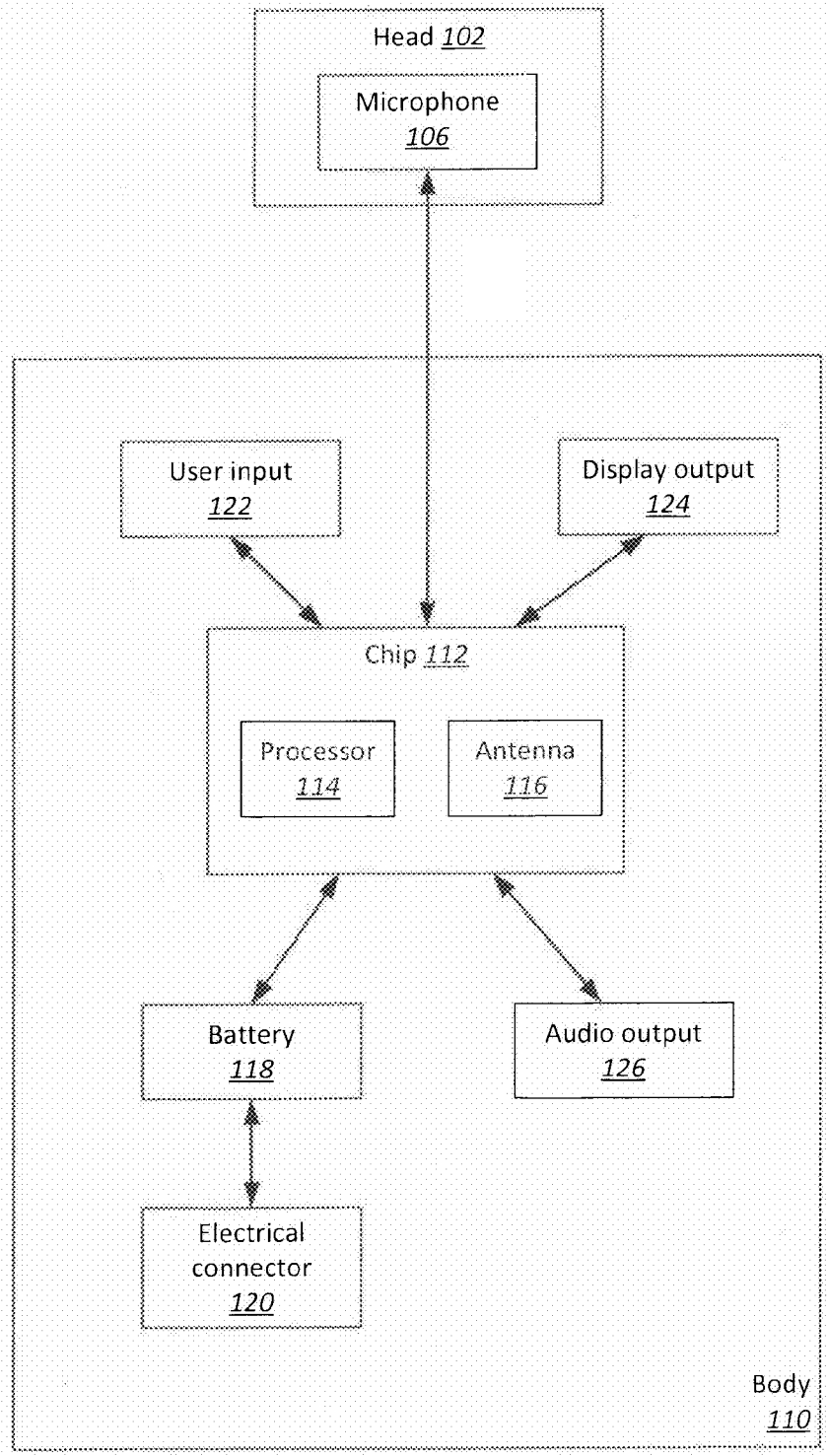
FIG. 2 illustrates a block diagram representing the components of the wireless stethoscope model of FIG. 1.

As shown in FIG. 2, the stethoscope body 110 includes a wireless transmission chip 112, which in some implementations may be a printed circuit board (PCB). The transmission chip 112 may include a processor 114 which is configured to control signals received from one or more microphones 106 disposed in the stethoscope head 102. The chip 112 may further include an antenna 116 which enables the device 100 to end and/or receive wireless signals. In some embodiments, the antenna 116 may be external to the chip 112.

The wireless chip 112 is also in electrical connection with a battery 118, which in some implementations may also receive power from an outside source by means of an electrical connector 120 disposed along the outside of the body casing. A user may connect an electrical adapter to the connector 120 in order to charge the battery 118.

The wireless chip 112 may also be in connection with one or more user inputs 122, such as buttons or switches, which in some implementations may be disposed along the outside of the body casing. Examples of inputs 122 include a power button, a button for establishing a wireless connection, and a volume control. The body 110 may also include one or more display outputs 124 such as indicator lights. In some implementations a display screen capable of showing words or images may also be included as display outputs 124.

The chip 112 may also be in communication with one or more audio outputs 126. Examples of audio outputs 126 include a speaker built into the body 110 or an audio jack for receiving an audio device. The audio output 126 may be configured to receive signals from the chip 112 and output those signals to a user. Audio signals may include device operation indicators such as beeps indicating operation, and may also include the data associated with sounds received by the microphone 106. If user inputs 122 include a volume control, the volume of the audio output 126 may be adjusted in accordance to signals received from the volume control.

The diaphragm 104 of the stethoscope head 102 aids in auscultation. The patient's internal body sounds are transmitted through the diaphragm 104, picked up by the microphone 106, and wirelessly sent to a mobile device by means of the wireless transmission chip 112. In addition to digitizing the signal for transmission, the microphone 106 may allow for the patient's internal body sounds to be amplified for better auscultation.

The chip 112 is capable of wirelessly transmitting an audio signal to the mobile device. The wireless stethoscope model 100 can use any appropriate communication means and protocol, such as Bluetooth short-range microwave signals or IEEE 802.11 compliant radio signals. In some implementations, the wireless stethoscope model 100 may be configured to pair directly to the mobile device. Alternatively, the wireless stethoscope 100 may communicate data to the mobile device through an intermediary device such as a wireless router maintaining a local area network (WLAN).

The stethoscope head 102 may be of any size or shape sufficient to detect the patient's internal body sounds. It may be comprised of metal, rubber, plastic, or another suitable polymer. The stethoscope head 102 is customarily around three to five inches in width and length. Although the head 102 and the diaphragm 104 are usually circular, other shapes may be used.

Figure 3:
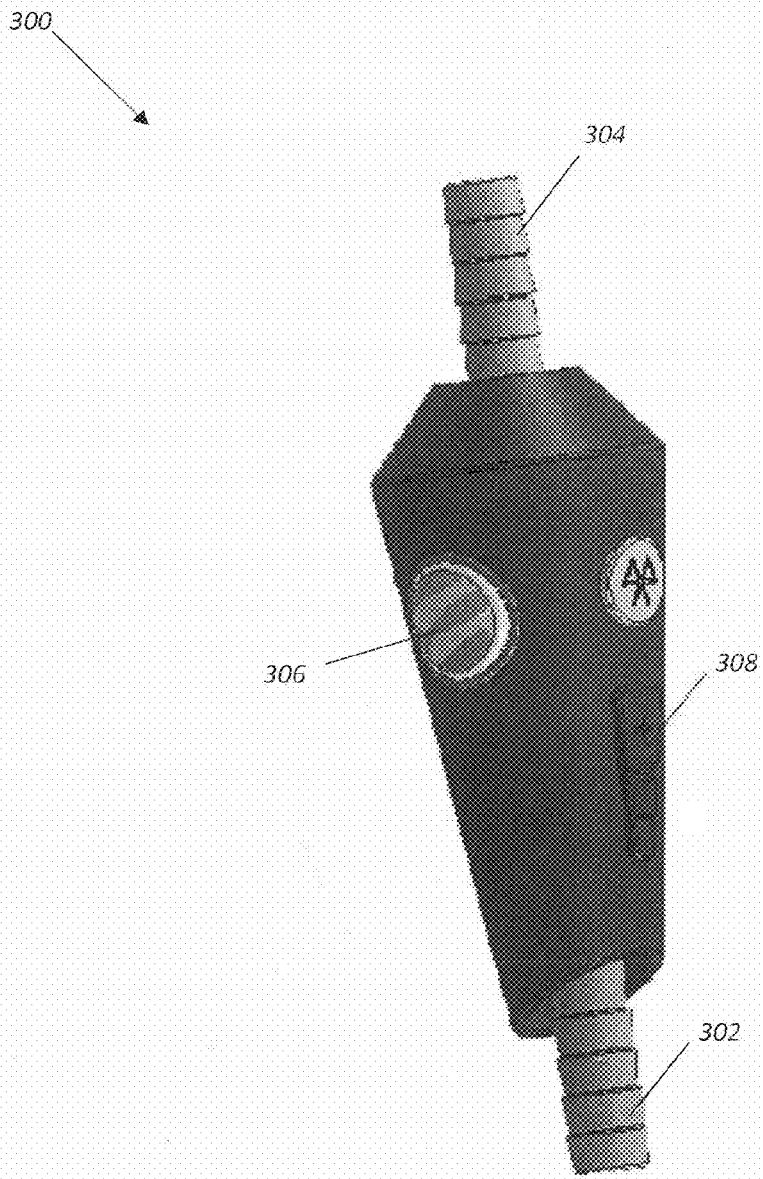
FIG. 3 is a perspective view of an in-line stethoscope adapter according to another embodiment of the present invention.

FIG. 3 shows an adapter 300 which may be used with a conventional acoustic stethoscope in order to perform the functions described herein with respect to the invention. The adapter 300 includes an air input tube 302 and an air output tube 304. The air input tube 302 can be connected to a conventional acoustic stethoscope head, such as the head 102 shown in FIG. 1. A stethoscope body with earpieces can be connected to the air output tube 304. The stethoscope user can place the stethoscope head on a patient's body and listen by means of the stethoscope earpieces as normal, but with additional features as described below. The adapter 300 may also include a switching valve 306 and volume controls 308.

Figure 4:
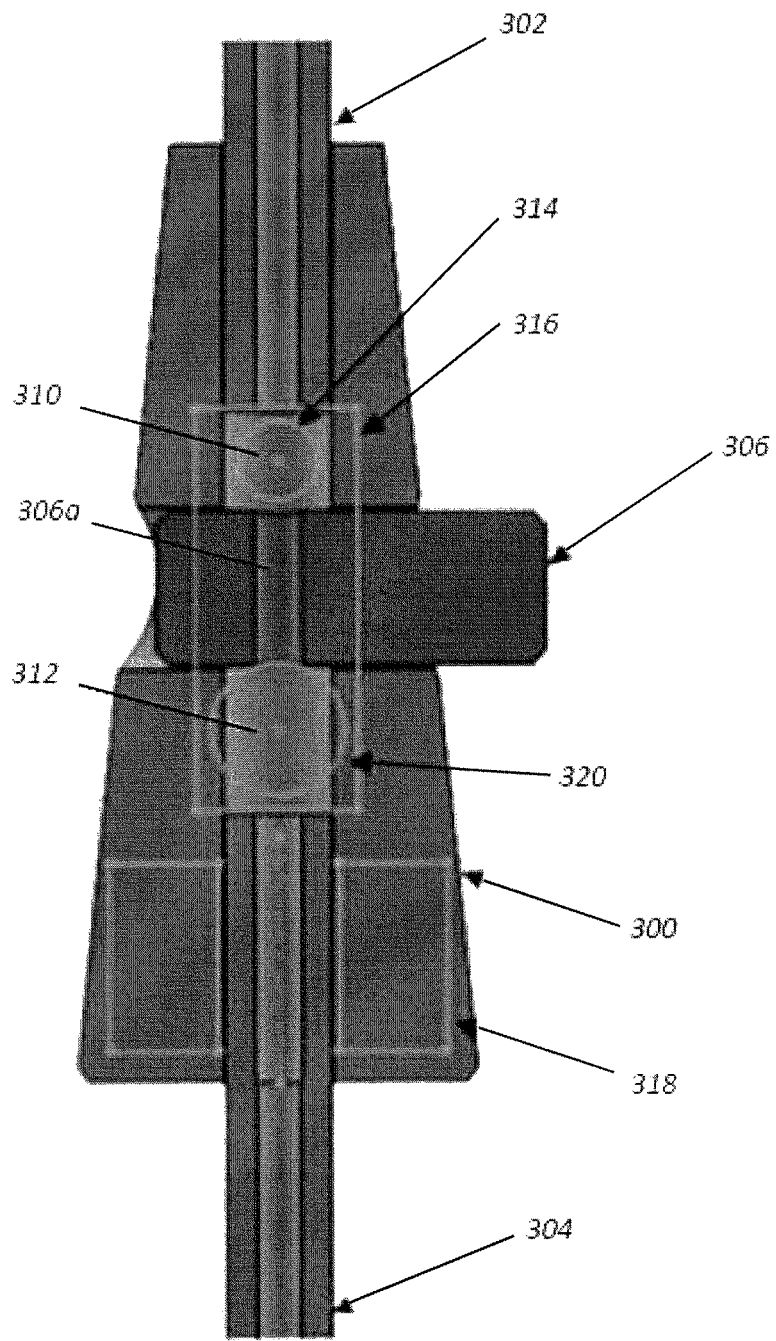
FIG. 4 is a cross-sectional view of the in-line stethoscope adapter of FIG. 3.

FIG. 4 shows a cross-sectional view of the adapter 300 in acoustic mode. Air input tube 302 is in fluid communication with a microphone chamber 310 which conducts sound from the tube 302. Similarly, the air output tube 304 is in fluid communication with a speaker chamber 312. The switching valve 306 can be positioned in either of two positions in order to alternate the adapter 300 between digital and acoustic modes. When in position for the acoustic mode, as shown in FIG. 4, an airway 306a disposed within the switching valve 306 connects the chambers 310, 312. This allows sounds which are gathered by the stethoscope head and conducted into the air input tube 302 to move through the microphone chamber 310, through the airway 306a, through the speaker chamber 312, and through the air output tube 304 into a stethoscope body and earpieces.

Outline 314 represents the position of a microphone which is positioned within the microphone chamber 310 such that it can detect sounds within the chamber 310 without disrupting the further conduction of those sounds within the airways of the adapter 300. The microphone 314 is within electrical communication with a PCB, represented by outline 316, which in turn includes a processor and antenna for wirelessly transmitting the microphone signals to a mobile device as described herein. Other than the location of the microphone, the PCB 316 and how it interacts with other electrical components of the adapter 300 may generally match the descriptions of the wireless transmission chip 112 described with respect to FIG. 2. Outline 318 represents the location of a rechargeable battery.

Outline 320 represents a speaker, which in some implementations may only be used when the switching valve 306 is moved into a digital mode. Moving the switching valve 306 into a digital mode may involve moving the airway 306a out of position from between the chambers 310, 312 such that the two chambers are no longer in fluid communication, disrupting the acoustic flow along the adapter 300.

While in digital mode, in addition to wirelessly transmitting the sound data sent from the microphone 302 to a connected mobile device, the PCB 316 also outputs the sounds data to the speaker 320, which is positioned within the speaker chamber 312 to direct sounds into the air output tube 304 without disrupting the acoustic flow through the chamber 312. In some implementations, the sound data sent to the speaker 320 may be adjusted by the PCB 316; for example, the sounds may be amplified or noise-reduced. A listener may be able to use the volume controls 308 to control the level of amplification by the PCB 316.

Figure 5:
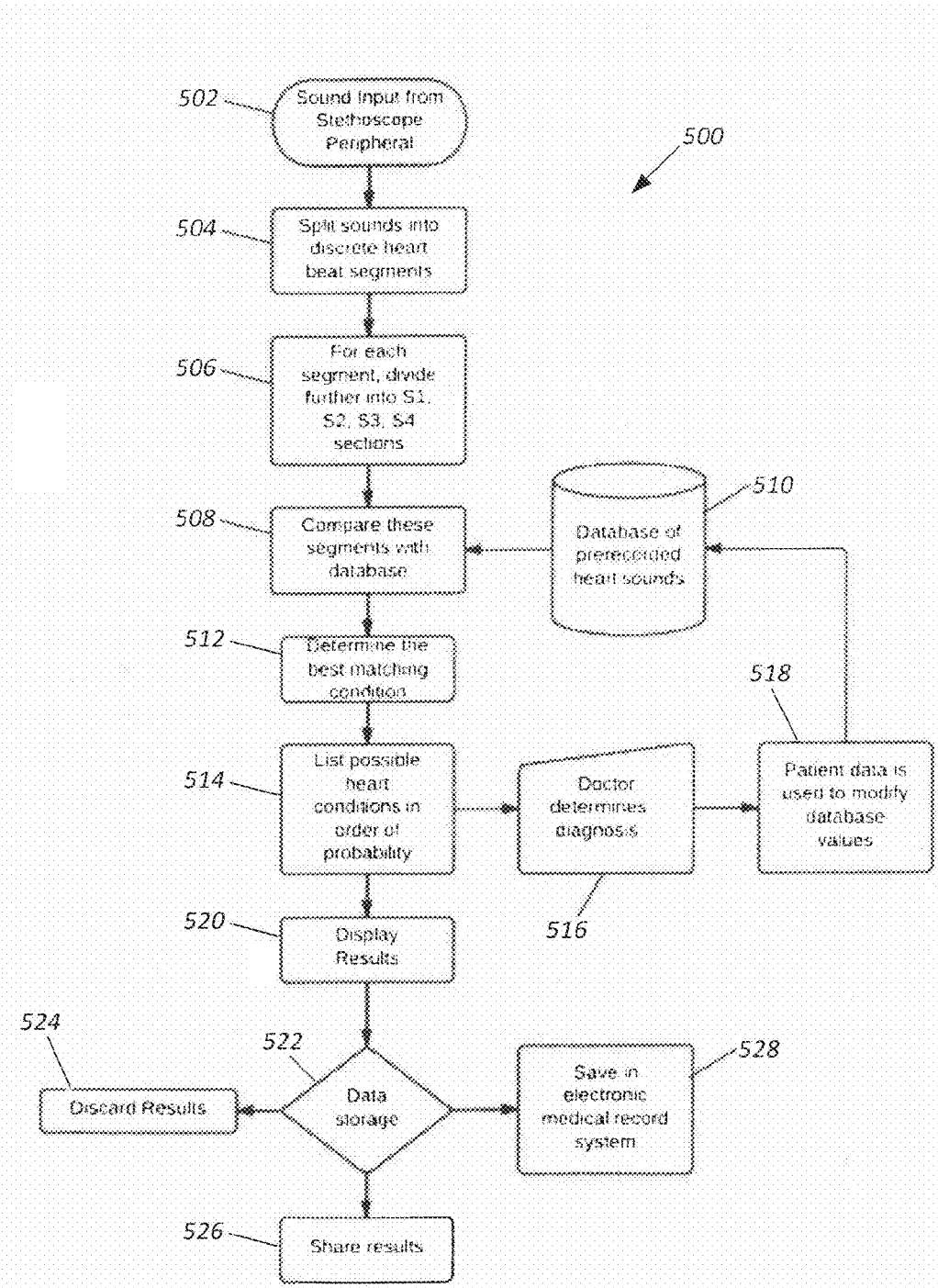
FIG. 5 is a schematic diagram illustrating a method for detecting and analyzing sounds according to an embodiment of the present invention.

FIG. 5 illustrates a method 500 for analyzing heart sound data received from a wireless stethoscope. The steps described herein may be carried out by a mobile device such as a smartphone or tablet used by a medical professional such as a doctor. It should be understood that, although the software carrying out many of the steps of this method 500 may provide useful data to the medical professional, a professional with appropriate training and certification should make any medical diagnosis.

Although the present example is specific to heart sound data, one of ordinary skill will recognize that condition matching is also possible for other internal patient sounds, such as respiratory or digestive sounds captured by a stethoscope.

Sound data is transmitted from the wireless stethoscope and received by the mobile device (502). The sound data may be in any format for storing audio data, and in some implementations may be immediately converted and displayed visually on the screen of the mobile device.

The received sounds may be split into segments each representing a heartbeat (504). Heartbeats may be recognized by short, distinct maxima in amplitudes accompanying the rapid closing of the valves of the heart. Each segment may be further divided into sections (506), which in some implementations may match sound sections typically recognized as part of the heart sound cycle (S1-S4).

Once the sound data is split up into segments and each segment further divided into sections, the sound data may then be compared to profiles in a database 510 of prerecorded heart sounds (508). The database 510 may include genuine recordings of heart sounds as well as simulated "model" heart sounds, and each may be associated with one or more conditions. Profiles may also include demographic data that may be relevant to matching, such as age, gender, and weight range of the patient associated with a particular set of heart sounds.

In some implementations, the comparison may be carried out by converting the sound data in each section into a matrix of values, which may then be graphed as a spectrogram using a short-time Fourier transform. Important locations of interest signified by the local minima and maxima are compared with the database 510 of previously recorded and analyzed samples, which have received similar treatment. Statistical techniques such as linear regressions, Bayesian analysis, and machine learning algorithms may be used to match the input sound with the database 510

In some implementations, at least some of the computer processing involved in converting and comparing the data may not occur within the mobile device itself. For example, the mobile device may transmit the data to a remote application server which is in communication with the mobile device through a network such as the Internet. The application server may provide some or all of the analysis of the data, including accessing the database, and transmit the results of its operations back to the mobile device. That way, much of the analysis may be performed remotely and less data transfer and processing power is needed by the mobile device itself. In other implementations, some or all of the processing may be performed locally by the mobile device itself.

Based on comparing the sound data to the sample data in the database, the system determines one or more matching conditions (512). As some of the database samples may involve regular heartbeats, "regular" may be one of the matched conditions.

The conditions are presented on the mobile device to the doctor or other medical professional in order of likelihood based on the analysis (514). In some implementations, additional data may be made available to the doctor on the mobile device, such as a visual graph showing the analyzed sound data against the relevant match among the prerecorded data, or one or more values representing the strength of the match (the r-value of a linear regression, for example).

A doctor reviews the results and makes a diagnosis (516), which may then be used to modify database values (518). For example, if the database engages in machine learning for various parameters of prerecorded data, the parameters may be adjusted based on the conditions that the doctor has concluded should be associated with the sound data. In some implementations, one or more segments of the patient's sample may be added to the database associated with the diagnosed conditions.

Once the analysis is performed, the doctor may later display, save, discard, share, remotely access, and export the results (520-528). These functions may be carried out by means of an application installed on the mobile device, which may in turn communicate with a mobile server capable of receiving results and storing them to a remote accessible location. The results may be associated with a particular patient and doctor within the system, and may be accessed by that doctor and exported to other medical systems with explicit authorization by that doctor. The doctor may later pull the patient data as part of a medical assessment of the patient or when reviewing the patient's records.

Figure 6:
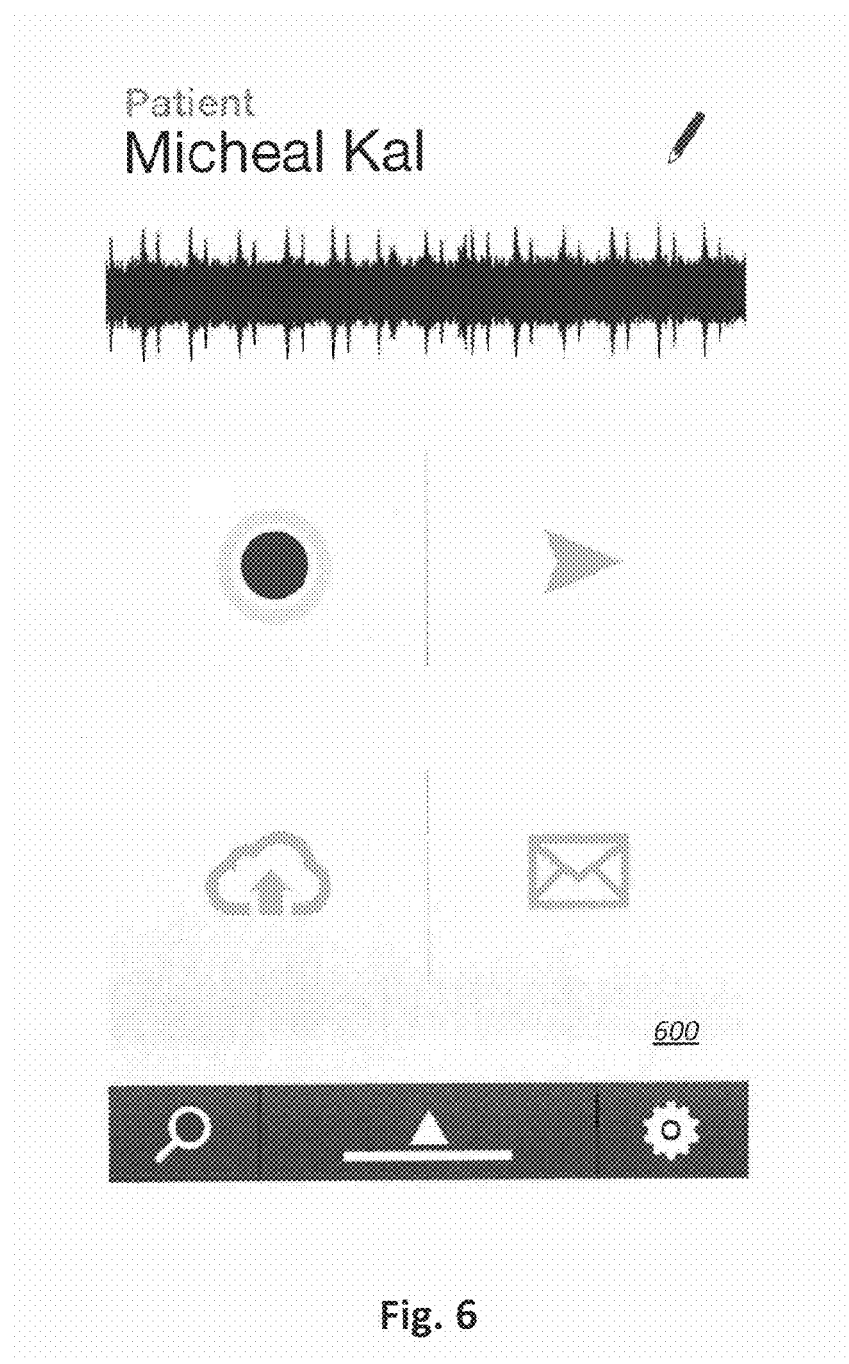
FIG. 6 is a screenshot of a mobile device application according to an embodiment of the present invention.

FIG. 6 shows an example of a screenshot 600 from a mobile device application for analyzing sound data. The mobile device application may include a variety of features, such as the ability to start and stop a new recording of patient sound data received from the wireless stethoscope. The mobile device may be able to associate data with particular patients and to play back previously-recorded sound data. Charts of sound data and of analysis may also be displayed on the mobile device as described above. From the mobile device, a doctor may be able to save recorded sound data to a remote server or to send sound data to a particular system or to another doctor.

Embodiments of the invention may be performed by means of software, which may in turn involve the processing of input data and the generation of output data to some extent. For example, specific electronic components may be employed in a mobile device processor or similar or related circuitry for implementing the functions associated with receiving and analyzing patient sound data in accordance with the present disclosure described above. Alternatively, one or more processors operating in accordance with instructions may implement the functions associated with receiving and analyzing patient sound data in accordance with the present disclosure as described above. If such is the case, it is within the scope of the present disclosure that such instructions may be stored on one or more non-transitory processor readable storage media (e.g., a magnetic disk or other storage medium), or transmitted to one or more processors via one or more signals embodied in one or more carrier waves.

Although the invention has been described and illustrated in the foregoing illustrative embodiments, it is understood that the present disclosure has been made only by way of example, and that numerous changes in the details of implementation of the invention can be made without departing from the spirit and scope of the invention. Features of the disclosed embodiments can be combined and rearranged in various ways.

What is claimed is:

1. An apparatus for a wireless stethoscope device, comprising:
   an airway comprising a first chamber and a second chamber in fluid communication, the airway permitting the acoustic transmission of sound between an input tube sized for interface with a stethoscope head and an output tube, wherein the first chamber and the second chamber are disposed between the input tube and the output tube, and are external to the stethoscope head;
   a microphone disposed in the first chamber of the airway, the microphone configured to detect sounds picked up by the stethoscope head and transmitted acoustically into the airway without blocking further acoustic transmission of sound through the airway to the output tube;
   a wireless transmitter in communication with the microphone, the wireless transmitter configured to receive sound data detected by the microphone and transmit the sound data wirelessly to a mobile device;
   a switching valve disposed within the airway, the switching valve configured to permit acoustic transmission of sound in an open position corresponding to an acoustic mode of operation for the wireless stethoscope device, and block acoustic transmission of sound in a closed position corresponding to a digital mode of operation for the wireless stethoscope device; and
   a speaker disposed in the second chamber of the airway between the switching valve and the output tube, the speaker configured to permit acoustic transmission of sound down the airway when the wireless stethoscope device is in the acoustic mode of operation and to provide sounds for transmission to the output tube when the wireless stethoscope device is in the digital mode of operation;

wherein the first chamber is between the input tube and the switching valve such that the microphone detects sounds transmitted from the input tube when the valve is closed, and wherein the wireless transmitter transmits sound data in both the acoustic mode of operation and the digital mode of operation.

2. The apparatus of claim 1, wherein the speaker amplifies sounds received by the microphone when the wireless stethoscope device is in digital mode.

3. The apparatus of claim 2, wherein the apparatus further comprises a volume control configured to adjust the speaker volume when the stethoscope device is in digital mode.

4. The apparatus of claim 1, wherein the apparatus is configured as a single modular component to be placed between a conventional acoustic stethoscope head and body in order to convert a conventional acoustic stethoscope into a wireless stethoscope device.

5. A computer-implemented method for detecting and analyzing sounds received from a wireless stethoscope device, comprising:
  receiving, at a processor in a mobile device, heart sound data from a patient that is wirelessly transmitted from a wireless stethoscope device;
  splitting, at the processor in the mobile device, the heart sound data into a plurality of segments each representing a heartbeat;
  splitting, at the processor in the mobile device, each of the plurality of segments into a plurality of sections each representing a heart sound cycle;
  comparing, at the processor in the mobile device, the heart sound data based on the plurality of segments and the plurality of sections to the profiles in the database of pre-recorded sounds, wherein each pre-recorded sound is associated with at least one condition;
  determining, at the processor in the mobile device, at least one of the pre-recorded sounds that matches the heart sound data; and
  displaying, on a display in the mobile device, the at least one condition associated with the at least one of the pre-recorded sounds that matches the heart sound data;
  wherein the wireless stethoscope device comprises:
    an airway comprising a first chamber and a second chamber in fluid communication, the airway permitting the acoustic transmission of sound between an input tube sized for interface with a stethoscope head and an output tube, wherein the first chamber and the second chamber are disposed between the input tube and the output tube, and are external to the stethoscope head;
    a microphone disposed in the first chamber of the airway, the microphone configured to detect sounds picked up by the stethoscope head and transmitted acoustically into the airway without blocking further acoustic transmission of sound through the airway to the output tube;
    a wireless transmitter in communication with the microphone, the wireless transmitter configured to receive sound data detected by the microphone and transmit the sound data wirelessly to a mobile device;
    a switching valve disposed within the airway, the switching valve configured to permit acoustic transmission of sound in an open position corresponding to an acoustic mode of operation for the wireless stethoscope device, and block acoustic transmission of sound in a closed position corresponding to a digital mode of operation for the wireless stethoscope device; and
    a speaker disposed in the second chamber of the airway between the switching valve and the output tube, the speaker configured to permit acoustic transmission of sound down the airway when the wireless stethoscope device is in the acoustic mode of operation and to provide sounds for transmission to the output tube when the wireless stethoscope device is in the digital mode of operation;
    wherein the first chamber is between the input tube and the switching valve such that the microphone detects sounds transmitted from the input tube when the valve is closed, and wherein the wireless transmitter transmits sound data in both the acoustic mode of operation and the digital mode of operation.

6. The method of claim 5, further comprising:
  receiving, at the processor in the mobile device, respiratory sound data or digestive sound data from the patient that is wirelessly transmitted from the wireless stethoscope device;
  comparing, at the processor in the mobile device, the respiratory sound data or the digestive sound data to the profiles in the database of the pre-recorded sounds;
  determining, at the processor in the mobile device, a second one of the pre-recorded sounds that matches the respiratory sound data or the digestive sound data; and
  displaying, on the display in the mobile device, at least one condition associated with the second one of the pre-recorded sounds that matches the respiratory sound data or the digestive sound data.

7. The method of claim 5, wherein receiving the heart sound data from the patient further comprises:
  converting, at the processor in the mobile device, the heart sound data in a format suitable for visually displaying the heart sound data; and
  displaying, on the display in the mobile device, the converted heart sound data.

8. The method of claim 5, further comprising storing at least one of genuine recordings of heart sound data or simulated model heart sound data as the pre-recorded sounds in the database.

9. The method of claim 5, further comprising:
  receiving, at the processor in the mobile device, a diagnosis of the at least one condition associated with the at least one of the pre-recorded sounds that matches the heart sound data; and
  modifying data in the database based on the received diagnosis.

10. A computer-implemented method for detecting and analyzing sounds received from a wireless stethoscope device, comprising:
  receiving, at a remote application server, heart sound data from a patient that is wirelessly transmitted from a wireless stethoscope device via a mobile device;
  splitting, at the remote application server, the heart sound data into a plurality of segments each representing a heartbeat;
  splitting, at the remote application server, each of the plurality of segments into a plurality of sections each representing a heart sound cycle;
  comparing, at the remote application server, the heart sound data based on the plurality of segments and the plurality of sections to the profiles in the database of pre-recorded sounds, wherein each pre-recorded sound is associated with at least one condition;

determining, at the remote application server, at least one of the pre-recorded sounds that matches the heart sound data; and transmitting, from the remote application server, information on the at least one condition associated with the at least one of the pre-recorded sounds that matches the heart sound data to the mobile device for display;

wherein the wireless stethoscope device comprises:
- an airway comprising a first chamber and a second chamber in fluid communication, the airway permitting the acoustic transmission of sound between an input tube sized for interface with a stethoscope head and an output tube, wherein the first chamber and the second chamber are disposed between the input tube and the output tube, and are external to the stethoscope head;
- a microphone disposed in the first chamber of the airway, the microphone configured to detect sounds picked up by the stethoscope head and transmitted acoustically into the airway without blocking further acoustic transmission of sound through the airway to the output tube;
- a wireless transmitter in communication with the microphone, the wireless transmitter configured to receive sound data detected by the microphone and transmit the sound data wirelessly to a mobile device;
- a switching valve disposed within the airway, the switching valve configured to permit acoustic transmission of sound in an open position corresponding to an acoustic mode of operation for the wireless stethoscope device, and block acoustic transmission of sound in a closed position corresponding to a digital mode of operation for the wireless stethoscope device; and
- a speaker disposed in the second chamber of the airway between the switching valve and the output tube, the speaker configured to permit acoustic transmission of sound down the airway when the wireless stethoscope device is in the acoustic mode of operation and to provide sounds for transmission to the output tube when the wireless stethoscope device is in the digital mode of operation;

wherein the first chamber is between the input tube and the switching valve such that the microphone detects sounds transmitted from the input tube when the valve is closed, and wherein the wireless transmitter transmits sound data in both the acoustic mode of operation and the digital mode of operation.

11. The method of claim 10, further comprising:
receiving, at the remote application server, respiratory sound data or digestive sound data from the patient that is wirelessly transmitted from the wireless stethoscope device via the mobile device;

comparing, at the remote application server, the respiratory sound data or the digestive sound data to the profiles in the database of the pre-recorded sounds;

determining, at the remote application server, a second one of the pre-recorded sounds that matches the respiratory sound data or the digestive sound data; and transmitting, from the remote application server, information on at least one condition associated with the second one of the pre-recorded sounds that matches the respiratory sound data or the digestive sound data to the mobile device for display.

12. The method of claim 10, wherein receiving the heart sound data from the patient further comprises:
converting, at the remote application server, the heart sound data in a format suitable for visually displaying the heart sound data; and transmitting, from the remote application server, the converted heart sound data to the mobile device for display.

13. The method of claim 10, further comprising storing at least one of genuine recordings of heart sound data or simulated model heart sound data as the pre-recorded sounds in the database.

14. The method of claim 10, further comprising:
receiving, at the remote application server, a diagnosis of the at least one condition associated with the at least one of the pre-recorded sounds that matches the heart sound data from the mobile device; and modifying data in the database based on the received diagnosis.

\* \* \* \* \*